United States Patent [19]

Menger et al.

[11] Patent Number: 4,845,034

[45] Date of Patent: * Jul. 4, 1989

[54] BIOCHEMICALLY REACTING SUBSTRATES IN SUBTERRANEAN CAVITIES

[75] Inventors: William M. Menger; Ernest E. Kern, both of Houston, Tex.; Kermit Allen, Tulsa, Okla.; O. C. Karkalits, Lake Charles, La.; Donald L. Wise, Belmont; Alfred P. Leuschner, Ipswich, both of Mass.

[73] Assignee: Houston Industries Incorporated, Houston, Tex.

[*] Notice: The portion of the term of this patent subsequent to May 2, 2006 has been disclaimed.

[21] Appl. No.: 816,289

[22] Filed: Jan. 6, 1986

Related U.S. Application Data

[63] Continuation-in-part of Ser. No. 693,028, Jan. 22, 1985.

[51] Int. Cl.4 ............................................. C12P 5/02
[52] U.S. Cl. .................................... 435/167; 210/603; 210/630; 48/210; 585/943
[58] Field of Search ............... 435/167; 210/603, 630; 48/210; 585/943

[56] References Cited

U.S. PATENT DOCUMENTS

| | | | |
|---|---|---|---|
| 3,185,216 | 5/1965 | Hitzman | 166/42 |
| 3,826,308 | 7/1973 | Compere-Whitney | 166/246 |
| 4,518,399 | 5/1985 | Croskell et al. | 210/603 |

Primary Examiner—Charles F. Warren
Assistant Examiner—Carolyn S. Greason
Attorney, Agent, or Firm—Pravel, Gambrell, Hewitt, Kimball & Krieger

[57] ABSTRACT

A method for carrying out a biochemical reaction with a culture of microorganisms is performed in a cavity formed in a subterranean formation to produce combustible hydrocarbon gases. The method is especially suitable for the conversion of alkali-oxidized or hydrolyzed coal, such as lignite, to methane. The method may be performed in the cavity as a continuously stirred tank reaction, or plug flow or as a staged reaction. The method may also be done as an anaerobic fixed film process using particles as an anaerobic filter, as a sludge blanket, or as an expanded bed process.

8 Claims, 3 Drawing Sheets

BIOCHEMICALLY REACTING SUBSTRATES IN SUBTERRANEAN CAVITIES

CROSS-REFERENCE TO RELATED APPLICATION

The present application is a continuation-in-part of U.S. patent application Ser. No. 693,028, filed Jan. 22, 1985 and copending herewith.

FIELD OF INVENTION

This invention relates to utilizing subterranean cavities formed for the purposes of biochemically reacting a substrate placed therein. More particularly, this invention relates to producing useful products by the growth of microorganisms in a substrate placed in a cavity formed in a subterranean salt formation, limestone, or other earthen rock or sandstone formations.

DESCRIPTION OF THE PRIOR ART

Many useful products have been obtained by the action of microbial organisms from the digestion of carbohydrates by microorganisms, such products including ethanol, insulin by man-made microorganisms, and methane from the anaerobic digestion of biomass. Because of the slow growth or action of the microbes, it is often necessary to use a large reactor to produce biochemical products in usable quantities. Often, startup times ranging up to several months are required for the microbes to grow to achieve a sufficient population density in the substrate to produce usable quantities of the desired biochemical products. Further, conditions for the microorganisms, including temperature, pH and toxic substance concentrations, must be maintained within critical limits to avoid killing the microbes. Thus, if such conditions are not maintained, mortality of the microorganisms will result and their growth must be reinitiated.

In the conversion of biomass to methane in commercially significant quantities, the above problems are particularly acute because of the large volumes of biomass and methane involved. Much effort has been directed to providing suitably economic reactors for the conversion of biomass into methane. For example, U.S. Pat. No. 4,356,269 describes a semisubmerged insulated apparatus which has a preheating chamber provided with a heating device, a gas processing chamber in which the microorganisms are grown, and a storage chamber for spent manure.

The anaerobic digestion of biomass is typically a three-step process in which complex organic materials are converted to the end products of methane and carbon dioxide. In the initial steps, complex organic molecules are converted into organic acids such as propionate, butyrate, valerate, lactate, formate and ethanol, and eventually into acetate. The organisms responsible for this conversion are collectively termed acid formers and may be either anaerobic or facultative in nature. The final step, conversion of acetate to methane and carbon dioxide, is performed by organisms collectively termed methane formers, or methanogens, which are strictly anaerobic. Because the methanogens generally grow more slowly than do the acid formers, the final step of the process is considered the rate limiting step. Generally, conversion of a complex organic substrate yields a gas which is typically sixty to seventy percent methane and thirty to forty percent carbon dioxide.

Reactor environmental parameters of concern for providing proper anaerobic digestion conditions include temperature, pH, alkalinity, volatile acid concentrations, nutrients, and toxic substances. These environmental parameters must be controlled within specific ranges for adequate digestion to occur, especially due to the sensitivity and slow growth of methane formers.

Three general temperature ranges exist for anaerobic fermentation, psychrophilic (10° to 20° C.), mesophilic (30° to 40° C.), and thermophilic (50° to 60° C.). Generally, anaerobic digesters are operated in the mesophilic or thermophilic temperature ranges because of the higher digestion rates. In the anaerobic digesters heretofore known, heat is carefully supplied to maintain the appropriate temperature. If the temperature is too low, the digestion rate is unsatisfactory. On the other hand, if the temperature is too high, the microorganisms may be killed. Only in systems operating in the psychrophilic range with extremely high microbial densities are the digesters operated without supplying heat.

The pH, alkalinity and volatile acid concentrations are interdependent. For stable anaerobic digestion to occur, the system pH should be between 6.6 and 7.6, with an optimum range of 7.0 to 7.2. Volatile acids, an intermediate product in the fermentation process, can increase in concentration if a system imbalance occurs due to other environmental factors which inhibit the growth of the methane formers. In such a situation, volatile acid concentrations will increase and the pH will drop, thus further aggravating the situation until the digester fails. Typically, this problem is avoided by properly buffering the digester with alkali to a near neutral pH.

A variety of organic and inorganic substances are required for adequate digestion to occur, including carbon, nitrogen, phosphorous, sulfur, vitamins and trace minerals. Organic materials deficient in one or more of these nutrients are typically supplemented. Generally, a weight ratio of carbon to nitrogen to phosphorous of 100:5:1 is adequate.

Numerous substances, if present in a high enough concentration, will pose inhibitory or toxicity problems in a digester. The substances of major concern include sulfides (greater than 200 mg/l), soluble heavy metals (greater than 1.0 mg/l), alkaline earth metals such as sodium (5000–8000 mg/l), potassium (4000–10,000 mg/l), calcium (2000–6000 mg/l), magnesium (1200–3500 mg/l), and ammonia (1700–4000 mg/l).

Conventional anaerobic digesters are of four classes. Completely mixed, single stage anaerobic digesters are the most common form of reactors used to stabilize organic materials and produce methane gas. These reactors have been used in treating municipal sewage, industrial waste, and agricultural residues. Generally, completely mixed digesters are maintained at a constant volume by feeding and withdrawing the same volume of influent and effluent. These digesters are agitated on an intermittent or continuous basis, depending upon the specific material being digested, and have a relatively long retention time of ten to thirty days. This system is typically used with residues having organic concentrations in excess of 10,000 mg/l of biological oxygen demand (BOD).

Although in theory this type of system can operate on a more dilute waste, the economics of conversion are unfavorable. Because of the long retention times and slow rate of substrate conversion, dilute wastes are not converted rapidly enough or to the degree necessary to produce enough methane to sustain the process. Moreover, the start up period required to achieve efficient steady state operation of a completely mixed, single stage anaerobic digester may be as long as a few months or more, depending upon the quantity of seed material initially placed in the digester and the retention time at which the system is operated.

Another type of digester, the anaerobic contact process, is a modification of the completely mixed, single stage anaerobic digester. As with the completely mixed, single stage anaerobic digester, the anaerobic contact process is operated in such a manner as to maintain a constant volume by adding substrate thereto and withdrawing effluent therefrom at equivolume rates. The effluent is fed to a clarifier in which biological solids are settled, withdrawn and recirculated into the digester. Some of the recycled solids are periodically removed from the system so that inert solids will not accumulate. The clarified liquid overflows from the clarifier and is discharged. In this manner, the hydraulic retention time of the digester can be minimized to less than a day while biological solids are retained in the system for significantly longer periods, ten days or more. Consequently, dilute concentrations of organic wastes can be converted to methane and carbon dioxide quickly in a reactor which is comparatively small with respect to the single stage system. The viability of the anaerobic contact process is dependent on the ability of the clarifier to separate the biological solids from the liquid to produce a low volume, highly concentrated recycled stream. Because the biological settling characteristics are substrate dependent, the system is not readily adaptable to a wide variety of substrates.

Another type of digester is the plug flow anaerobic digester in which the feed entering the reactor passes through the reactor as a discrete plug and each plug leaves the reactor in the same sequence in which it entered. Theoretically, each plug remains in the reactor for a period of time equal to the theoretical retention time and no internal mixing occurs. As each plug moves through the reactor, the microbial concentration will increase as the substrate concentration decreases. Hence, each plug of material can be considered a batch reactor travelling through the plug flow digester with time. Since the residue to be digested does not normally contain organisms required for digestion, each plug of feed will require inoculation with the required microbe. This inoculum is provided by recycling effluent solids from the effluent end of the digester back to the influent stream. Typically, as with the anaerobic contact process, clarification and solids recycling are employed.

Theoretically in ideal plug flow back mixing, sedimentation and flotation of solids and short-circuiting do not occur. However, in practice, ideal plug flow conditions are impossible to maintain. Plug flow conditions are approximated by providing a long, narrow, horizontal reactor and using a substrate which is viscous to inhibit particulate settlement or flotation, and which has a high concentration of solids. With this type of waste, clarification may be impossible. Typically, hydraulic retention times are on the order of ten to thirty days or more. As with the other systems, plug flow digesters require long start up times.

Yet another digester is the anaerobic packed bed digester which includes an elongated, vertical unit packed with an inert biological support medium such as gravel, Raschig rings, Berl saddles or the like. The liquid waste is introduced into the bottom of the reactor and removed from the top. The packing material provides a support or attachment surface for the anaerobic microbes. Hence, high concentrations of organisms can be maintained in the reactor, allowing for rapid conversion at lower temperatures. Because the organisms are attached to a fixed surface and occur in significantly higher concentrations than in other types of reactors, the units are highly stable and recover from toxic or hydraulic shock more readily than other systems. Generally, packed bed digesters are operated with hydraulic retention times of six hours to three days depending upon the substrate. Solids retention times will be significantly longer, up to 100 days or more, because the solids remain trapped in the bed and are not generally carried over with the effluent.

Other digesters which are exemplary of attempts to avoid the aforenoted problems include the in situ conversion of biomass reactants. For example, in U.S. Pat. No. 3,826,308 there is described a process in which a naturally occurring fossil fuel deposit was contacted in situ with an anaerobic fermenting microorganism. A more soluble intermediate product was formed which could be converted into organic acids by another microorganism. Yet another microorganism converted the organic acids into valuable products.

Another approach to in-situ recovery of petroleum from underground deposits utilizing microorganisms was that of U.S. Pat. No. 3,185,216. A well was drilled through adjacent petroleum bearing and water bearing formations, the water bearing formation was inoculated with a microorganism which grew at the oil-water interface to release the petroleum, and the well was then plugged back above the water formation after inoculation.

Similarly, U.S. Pat. No. 4,323,367 relates to a process for improved gas production and accelerated stabilization of landfills by in situ bioleaching of organic waste by acid-forming bacteria. The leachate was acted on by microorganisms in an acid phase digester. Part of the acid phase digester effluent was recirculated to the landfill to supply additional microorganisms and the remainder was used to produce methane from a methane phase digester.

It has also been known that caverns formed in subterranean salt domes, whether naturally occurring or otherwise formed, could be used for storing various materials, such as solid wastes (U.S. Pat. No. 3,665,716) and liquified gases (U.S. Pat. No. 4,140,423). Bacteria were introduced into the solid waste storage dome cavern to assist in refuse decomposition. U.S. Pat. No. 3,858,397 related to the use of caverns in salt domes to take advantage of their heat conducting characteristics for conducting heat promotable chemical reactions. Heat from the earth core was conducted by the salt dome to caverns. The cavern or caverns were located at depths where temperatures greater than the boiling point of water were present. At times, substantially higher temperatures, such as 200° C. to 250° C., were preferred. The thermal properties and conditions of salt dome caverns discouraged their consideration for use as vessels for biochemical reactions.

SUMMARY OF THE INVENTION

With the present invention, the aforementioned problems of prior art digesters are avoided by the growth of microorganisms under controlled temperature and pressure conditions in a substrate placed in a subterranean cavern or salt formation.

Briefly, the present invention is a method for carrying out a biochemical reaction which includes the steps of: placing a substrate suitable for the growth of microorganisms in a cavity formed in a subterranean cavern or salt formation; introducing a culture of microorganisms into the substrate; controlling conditions in the cavity to promote the growth of the microorganisms in the substrate; allowing the microorganisms to grow in the substrate in the cavity; and, recovering a biochemical product from the cavity which is formed by the growth of the microorganisms in the substrate in the cavity.

The method of the present invention broadly contemplates the production of useful products by the growth of microorganisms, those naturally occurring as well as genetically altered microbes, in suitable substrates. The method is particularly adaptable to microbially mediated biochemical reactions which require relatively large reactors to produce useable quantities of the desired products, such as the conversion of a substrate, typically coal in an aqueous alkali slurry enriched with nitrogen and phosphorous nutrients, to methane and other combustible hydrocarbon gases by anaerobic microorganisms. Preferably, the substrate to be converted has a weight ratio of nitrogen to carbon of at least 5:100, and of phosphorus to carbon of at least 1:100. Preferably, the microorganisms used to convert the substrate into methane include both acid formers and methanogens and the conditions of the substrate in the cavity include a pH between about 3 and about 10 and a temperature below about 100° C. for most known methanogenic bacteria (but up to 225° C. for some thermophiles). The products formed by the acid formers and methanogens in the substrate at such conditions are primarily methane, carbon dioxide and organic acids.

The reaction producing the gas products in the cavity is controlled and may take the form of a continuously stirred tank reaction, a staged reaction or a plug flow reaction. Also, the cavity may be packed with particles before the inoculated organic solution or mixture is introduced. This permits the reaction in the cavity to be in the form of an anaerobic fixed film process, which may be of the anaerobic filter, sludge blanket or expanded bed type of technique.

DETAILED DESCRIPTION OF THE PREFERRED EMBODIMENT

Figure 2:
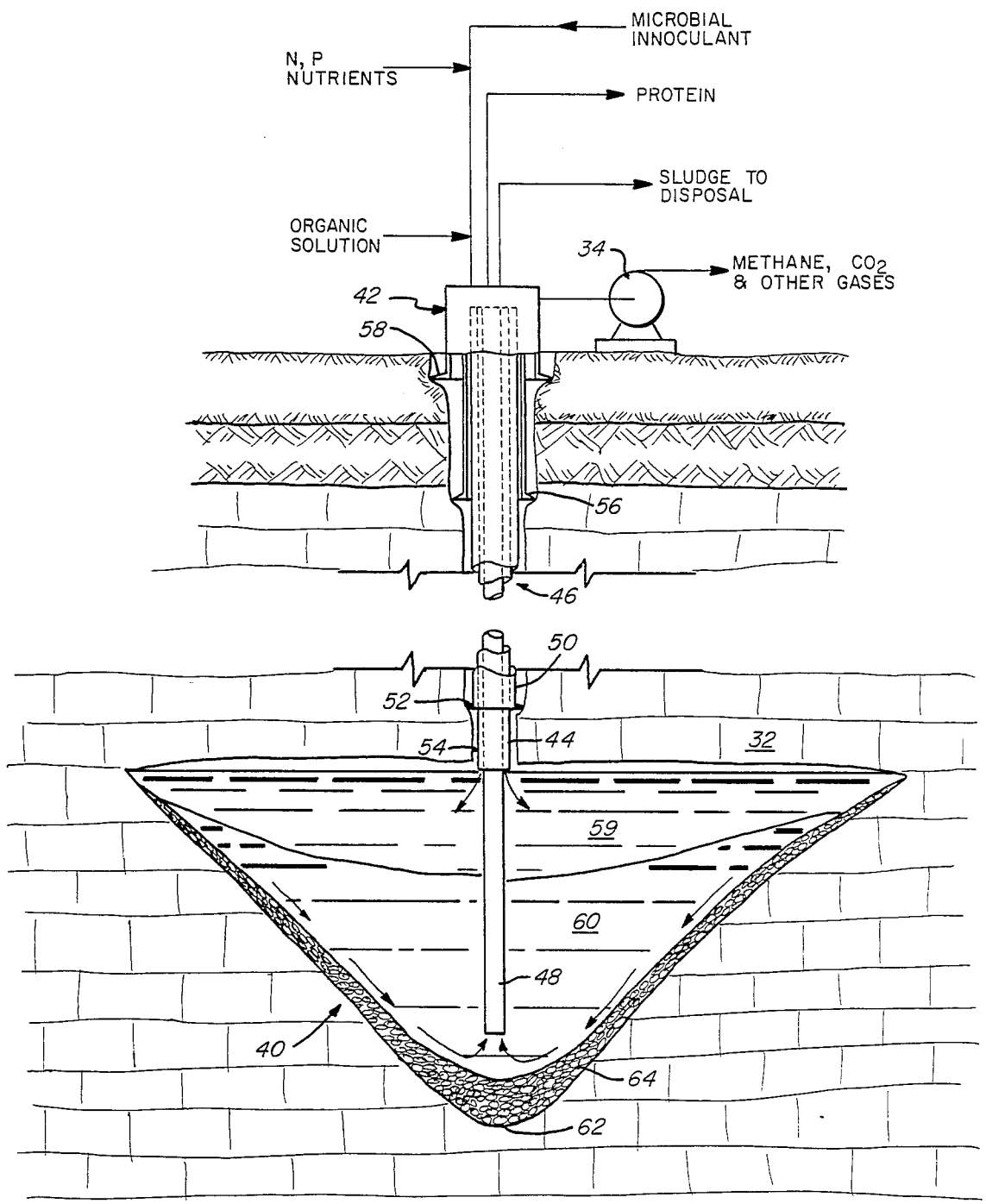
FIG. 2 is a schematic illustration of another embodiment of the present invention.
Figure 3:
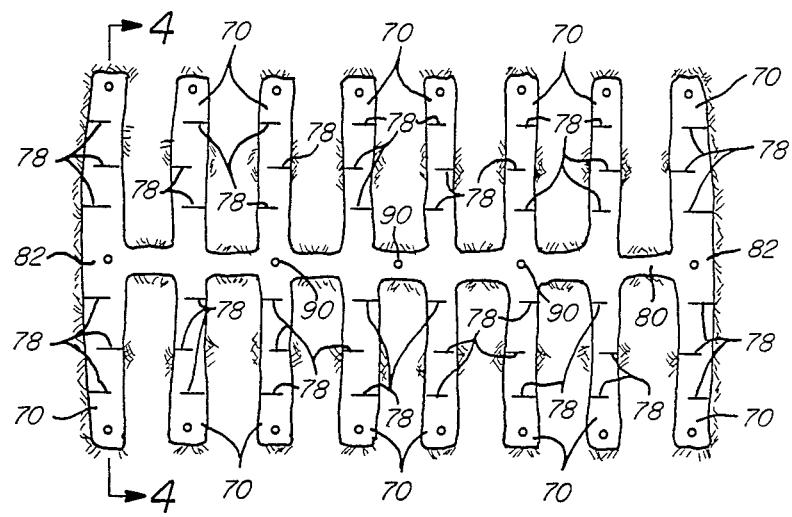
FIG. 3 is a plan view, partially broken away, of yet another embodiment of the present invention.
Figure 4:
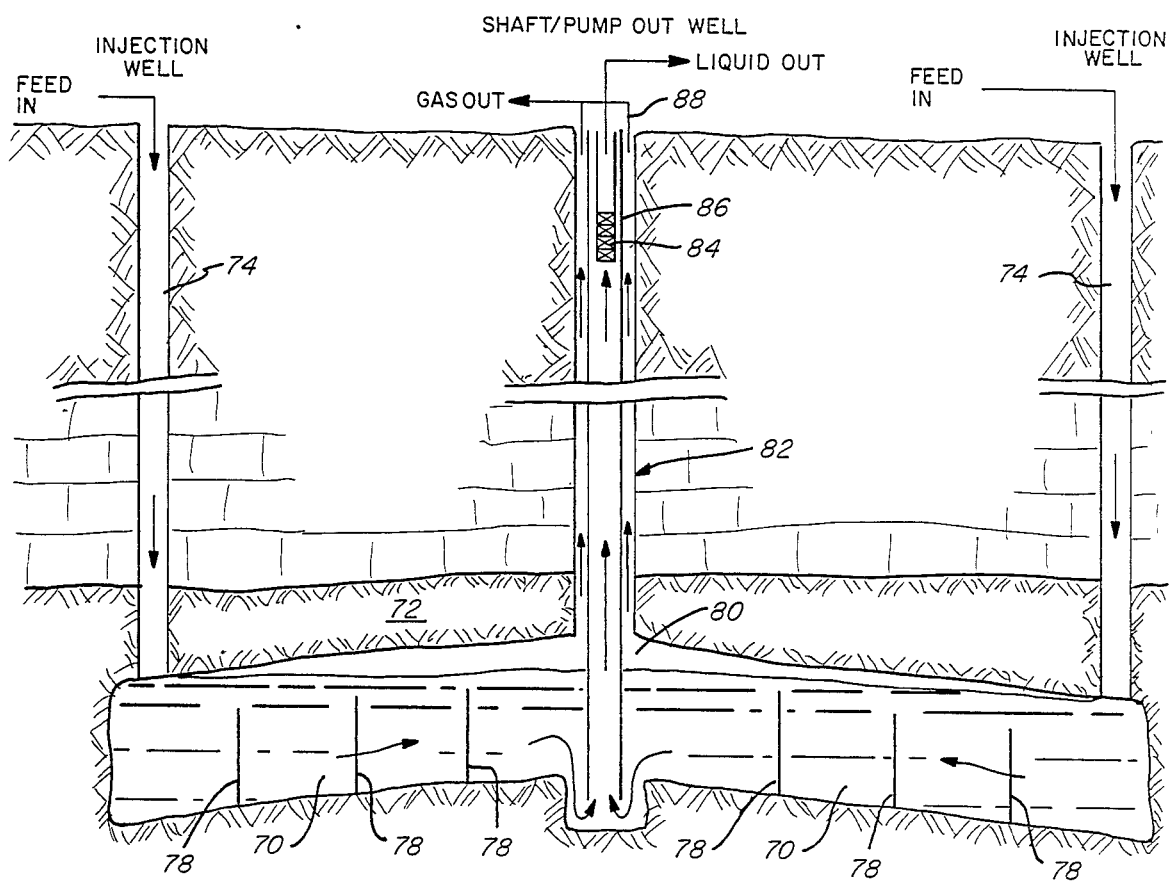
FIG. 4 is a cross-sectional view taken along the lines 4—4 of FIG. 3.

The method of the present invention may be carried out in either a cavity in a subterranean salt dome (FIGS. 1 & 2) or a chamber mined from a subterranean rock formation (FIGS. 3 & 4). In salt domes, the cavity may be a naturally occurring subterranean cavity or, more typically, in a cavity formed in a subterranean salt formation by well-known methods, such as solution mining. Because most microbially mediated biochemical reactions require moderate temperatures to sustain the microorganisms, it is preferred that the subterranean cavity or chamber be located at a shallow enough depth where the naturally occurring temperature coincides with the optimum temperature for the selected strain of microbes in order that the temperature of the substrate in the cavity can be maintained without cooling. When the present invention is to be performed in a mined chamber in a rock formation, the formation is selected after geological analysis has shown the formation to be suitable for maintaining dimensional integrity of the cavern, as well as to be free of fissures.

Suitable substrated in the method of the invention include solutions or pumpable suspensions of any organic material which satisfies the proper nutrient requirements for the microorganisms to be employed. It is also essential that the concentration in the substrate of substances toxic to the microorganisms to be employed remain sufficiently low to avoid mortality of the microorganisms. If the organic material to be used in the substrate is deficient in one or more nutrients, it may be rendered suitable for use as a substrate by the addition thereto of the appropriate nutrients. Likewise, it may be possible to remove toxic substances from a material to the extent that it is suitable for use as a substrate.

Depending on the conditions maintained in the substrate in the cavity, the use of virtually any known microorganism, either one naturally occurring or one formed by being genetically altered under laboratory conditions, is contemplated in the invention. For use in salt domes, the microorganisms must, of course, be salt tolerant. It may in some instances, however, not be possible to maintain the necessary conditions to sustain certain microorganisms in specific substrates and/or liquid media. For example, microorganisms which are sensitive to salt are not suitable for use in the invention is the salt concentration in the substrate or liquid medium is allowed to exceed lethal levels by the dissolving of salt from the walls of the cavity into the substrate. In some instances, however, this problem may be avoided by reducing the residence time of the substrate in the cavity, by reducing the solubility of salt in the liquid medium employed such as, for example, by maintaining a lower temperature or by addition thereto of a nontoxic substance which reduces the solubility of the salt therein, or by use of a liquid medium in which salt is not soluble. In many cases, it is believed that it will be within the capability of those skilled in the art to select or develop microorganisms which are relatively insensitive to salt.

For example it has been reported that certain cultures are capable of reducing sulfates and producing methane from carbon dioxide in salt marshes. Also, salt-tolerant anaerobic microbes have been recovered by Professor Zeikus (University of Wisconsin) from sediments in the Great Salt Lake, Utah. See, e.g., the article by Zeikus et al., "Isolation and Description of Haloanaerobriem prevalens gen. nov. and sp. nov., an obligately anaerobic halophile common to Great Salt Lake Sediments," Current Microbiology, Vol. 9, pp. 225–234 (1983).

There also appear to be other known sources of bacterial cultures to develop a community of organisms to accomplish coal gasification. They include sewage sludge bacteria; bacteria from areas such as Yellowstone Park which are tolerant of high temperatures and accustomed to a diet of substances including carbon and sulfur (Kargi et al., "Removal of sulfur Compounds from Coal by the Thermophilic Organism: Sulfolobus Acidocaldarius", Applied and Environmental Microbiology, Vol. 44, pp. 878–883, Oct. 1982); methane producing bacteria found naturally in petroleum formations at depths of from 5,000 to 20,000 feet and deeper, which can be collected from drilling mud at drilling rigs (Donaldson et al., "Conference Focuses on Microbial Enhancement of Oil Recovery", Oil and Gas Journal, Vol. 80, pp. 47–52, Dec. 20, 1982); and bacterial cultures or ecosystems found in fumaroles being investigated by the National Oceanographic Laboratory at La Jolla, California ("Geothermal Deep Sea Marine Life Now Found in Shallow Water", New York Times, June, 1984). In an illustrative embodiment described below, the temperature and pH ranges given are for one particular range of organisms insensitive to salt used in a subterranean salt cavity. The conditions described apply to conventional microorganisms which have evolved at or near the earth's surface at conditions similar to those present in the subterranean salt cavity or mined chamber. Depending on the organism selected, other cavities, temperature and pH ranges, and cavity depths could be used.

The substrate is placed in the subterranean cavity by appropriate means, including pumping or gravity flow, through a pipe or other suitable conduit communicating between the cavity and the surface. In the case of solid, insoluble organic material, the substrate may be placed in the cavity in the form of a liquid suspension. A culture of the microorganisms may be introduced into the substrate prior to placing it in the cavity. Alternatively, the inoculation may be accomplished by introducing the microbes directly into the cavity. Once the substrate and microorganisms are in place in the cavity, conditions in the substrate in the cavity which are suitable for promoting the growth of the microorganisms are controlled. If necessary, the substrate may be heated or cooled by circulation of the substrate from the cavity, heating or cooling the substrate at the surface and returning the heated or cooled substrate to the cavity. Alternatively, a heating or cooling medium may be circulated from the surface into the cavity in indirect heat exchange with the substrate and back to the surface. Preferably, the cavity is located at the proper depth to provide the optimum temperature without heating or cooling.

The pH of the substrate and the cavity may be controlled by periodic or continuous addition thereto of appropriate acids, bases or buffers. Similarly, the nutrients in the substrate may be supplemented by a periodic or continuous addition of deficient nutrients thereto. Likewise, the concentration of toxic substances in the substrate may be controlled by continuous or periodic addition thereto of neutralizing agents or by continuous or periodic removal of the substrate or biochemical products resulting from the growth or action of the microorganisms in the substrate. For example, where the growth of the microorganisms in a liquid substrate results in the formation of insoluble products, sediment may be removed from the lower portion of the cavity by means of a submerged sludge pump.

After the microorganisms and substrate have been in the cavity for a sufficient length of time at the proper conditions, biochemical products which are formed by the growth of the microorganisms in the substrate in the cavity are recovered. The product may be in the form of a gas, miscible or immiscible liquid, or soluble or insoluble solid, or a combination of these forms. Gas is removed from the upper portion of the cavity by means of a fan or compressor. Liquid or solid products are removed by pumping from appropriate depths in the cavity.

In an especially preferred embodiment of the invention, a substrate is anaerobically converted into methane. Preferably, the source of the substrate is coal. With the present invention, coal is used in the sense of carbonized vegetable material including peat, lignite, sub-bituminous coal, bituminous coal and anthracite coal. Lignite is the preferred substance due to its wide availability and its unsuitability for use in place of higher rank coal for certain purposes. Structurally, lignite is characterized by relatively low aromaticity, approximately 60% aromatic. The aromatic clusters of lignite are primarily one and two rings in contrast to bituminous coals having fused ring systems of 3 or more aromatics. In addition, lignite is characterized by a prevalence of oxygen-functional groups such as carboxylate, phenolic and ethereal components. Lignite also contains moisture and ash. The ash-containing portion of lignite contains both inorganics, such as calcium and sodium ions, and minerals, such as clay, pyrite and quartz. While the ash and moisture content may vary among lignites, the variation in the organic portion is not significant. As used herein, the term "lignite volatile solids" (LVS) refers to the organic portion of the lignite.

Figure 1:
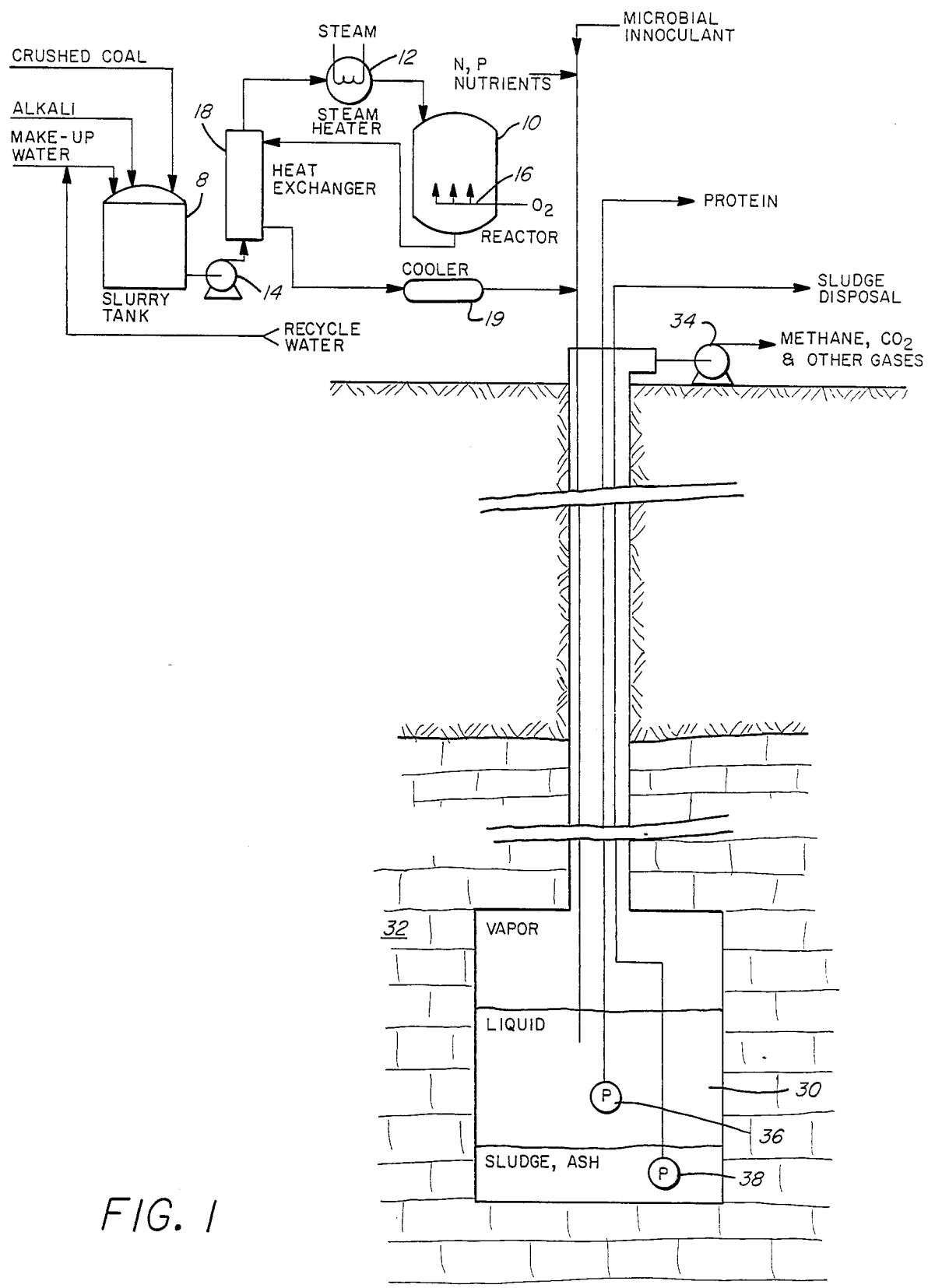
FIG. 1 is a schematic illustration of the method of the present invention in which coal is converted into methane and carbon dioxide in a cavity formed in a subterranean formation.

To render it suitable for use in the substrate, lignite is contacted in a finely divided state, i.e., substantially all particles less than about one-quarter inch, with a hot aqueous alkali solution and with or without oxygen in alkali hydrolysis vessel or reactor 10 as seen in FIG. 1. The crushed coal and alkali are mixed with water in a slurry prep tank 8 prior to heating and injection into the reactor 10 at elevated pressures. A temperature of from about 150° C. to about 300° C., preferably 200° C. to 250° C., is maintained in vessel 10 by preheating the feed to the reactor through heater 12. Pump 14 provides the pressure for the reaction.

The alkali used is not particularly critical and examples include potassium hydroxide, sodium hydroxide or sodium carbonate. The alkali is added to the crushed coal at a rate of from about 0.2 to about 20% on an LVS weight basis.

Oxygen can be introduced into vessel 10 by means of sparger 16 or other suitable means. The source of oxygen is preferably air, but may be purified oxygen. The amount of oxygen required is approximately 1 pound per pound LVS. A portion of the heat required to heat the alkali solution and the lignite is provided by the oxidation of the lignite. It should also be understood that in some instances, oxygen need not be used in the pretreatment step. In these situations, no sparger 16 need be present in the vessel 10.

The alkali oxidation of the lignite may be performed as a batch operation, but is preferably a continuous operation. In a continuous operation in which vessel 10 is continuously stirred, a residence time of 1.5 hours will result in a conversion of approximately 83% of the organic portion of the lignite into low molecular weight organics. The concentration of the organics in the liquid effluent from vessel 10 may be as high as 20% by weight or more. Preferably, the organic concentration is at least about 15% by weight.

The alkali hydrolized lignite solution is then cooled to lower the temperature down to about 35°–55° C. which is the preferred temperature for conducting the fermentation of the organics into methane. Cooling is performed in heat exchanger 18 preferably by heat exchange with the feed to vessel 10 and/or by cooling water in cooler 19. If desired, undissolved solids may be removed by filtration prior to anaerobic digestion. Alternatively, the solids may be removed from cavity 30 as a sludge which accumulates in the lower portion thereof.

Because lignite is normally deficient in nitrogen and phosphorus, these nutrients are added to the organic solution before it is introduced into the cavity 30. Suitable nutrient supplements are thus provided, which include potash and urea in amounts sufficient to result in a weight ration of nitrogen to carbon in the organic solution (typically) of about 5:100, and of phosphorus to carbon of about 1:100.

A microbial inoculant is also added at this time, in a form which includes acid formers and methanogens. The acid formers convert large organic molecules such as proteins, starches, and cellulose into organic acids and are anaerobic and/or facultative in nature. The methanogens convert the organic acids into methane and carbon dioxide and are strictly anaerobic. The microorganisms may be either psychrophilic, mesophilic or thermophilic.

The inoculated organic fluid solution or mixture is then fed via an influent pipe into cavity 30 formed in salt formation 32. The location of solution injection is preferably near the bottom of the cavity 30, but a suitable distance above bottom to allow room for ash and microbial sludge to accumulate. This is done in order to avoid physical removal of these solids during the service life of the cavern. If desired, a packed bed of crushed stone may be deposited on the cavity bottom to provide greater chemical reactant surface.

Conditions in the substrate are maintained such that the growth of the microorganisms therein is promoted. The temperature is maintained from about 10° C. to about 60° C., preferably 10°-20° C. for psychrophilic microorganisms, 30°-40° C. for mesophilic and 50°-60° C. for thermophilic. If necessary, the organic solution or mixture in the cavity may be heated or cooled as described above. The pH is maintained between about 6.5 and about 8.5, preferably between 6.6 and 7.6, and most preferably between 7.0 and 7.2. The pH may be continuously or periodically adjusted by addition of a mixture of acids or bases to the organic solution. However, buffering the organic solution or mixture with alkali at a near neutral pH will normally control the pH.

When the process of the present invention is performed in subterranean salt caverns, the biogasification reaction is preferably carried out in an aqueous broth containing greater than a 10% concentration of sodium chloride. Microbes are known to operate under anaerobic conditions at concentrations of 10°-20% sodium chloride. The use of broths with less than 10% sodium chloride requires special precautions to avoid or minimize leaching of sodium chloride from the cavern walls.

The microorganisms in the inoculated organic fluid solution or mixture are allowed to grow in the cavity for a sufficient period of time to convert a significant quantity of the organics into methane. The length of time required may range from one day to approximately thirty days, depending on the desired conversion rate and the specific substrate and conditions in the cavity. Methane and carbon dioxide are recovered from a vapor space at the top of the cavity through an effluent pipe by means of fan 34. The effluent and influent pipes can be on opposite sides (FIG. 1) of the cavity 30 so that the reacting liquid can be recirculated. The recovered gaseous mixture of methane and carbon dioxide may be subsequently processed to recover purified methane and carbon dioxide according to conventional processing methods.

A protein-rich broth may also be recovered by means of broth pump 36 and used for chemical feedstocks. Sediment may be removed from the cavity by means of sludge pump 38 or left in the cavity itself as an economical disposal alternative. The sludge contains insoluble lignite and/or solids formed by the growth of the microbes in the organic solution or mixture. The sludge can be disposed of or burned for fuel. A recirculation valve 40 is provided in the protein recovery line for recirculating the broth from broth pump 36, if desired.

In the embodiment set forth in FIG. 1, the microbial inoculant in the form of both acid formers and methanogens was added at one time with the cavity 30 functioning as a continuous stirred tank reactor. It should also be understood that a staged reactor design could also be used, with the acid formers being injected into a first vessel, whether at the surface or in a separate subterranean cavern or cavity. The methanogen components of the inoculant are then injected, along with the output of the first vessel, into the cavity 30 which serves as a second stage reactor.

In an alternative salt dome cavern embodiment of the present invention (FIG. 2), a generally conically shaped cavern 40 is formed in the salt dome formation 32. Cavern 40 functions as a continuously stirred tank reactor, receiving the alkali hydrolized lignite solution, nitrogen and phosphorous nutrients and microbial inoculant from structure like that of FIG. 1, which is for this reason not shown in FIG. 2.

In forming the cavern 40, raw water is fed at a wellhead 42 to a casing 44 of a string 46 of multiple concentric casings. Casing 44 is next innermost of the concentric casing string 46 and contains a longer, innermost wash casing 48. A product casing 50 is located concentrically about casing 44 and is sealed, as indicated schematically at 52, to form an annular pocket 54 in salt formation 32 about casing 44. A conventional intermediate casing 56 and conductor casing 58 complete the casing string 46.

During leaching operations, a compressed gas blanket is present in this pocket 54. A reverse circulation mining technique is used, and the raw water 59 entering cavern 40 from casing 44 mixes with and becomes a part of a brine wash 60 which leaches out the salt formation 32 to form the cavern 40. As leaching proceeds, wash casing 48 is gradually lowered with respect to casing 44, causing the cavern 40 to assume the general shape of a cone with a tip 62 at its lowermost central portion.

Once the cavern 40 has been formed of a suitable size, the brine and water are removed. The inoculated, nutrified solution to be fed to the cavern 40 is then injected through the casing 44 until cavern 40 is sufficiently charged. The microbial processes described with respect to FIG. 1 then are allowed to begin, with a cap of methane, carbon dioxide and other product gases accumulating in annular pocket 54. These gases are then withdrawn via product casing 50 by pump 34. The protein broth formed is withdrawn via wash casing 48. As the gases and broth are removed, new solution is added via casing 44.

An advantage of the conical cavern 40 is that any insoluble solids 64 produced during the biochemical reaction tend to fall and settle on downwardly sloping side walls of cavern 40, tending to migrate slowing toward the tip 62. These solids further coat the sloping walls of the cavern 40, acting as a barrier to inhibit additional leaching during operation of cavern 40 as a continuously stirred tank bioreactor. The solids by moving downwardly also move away from the gas removal pocket 54 at the top of cavern 40, facilitating the gas-liquid separation process.

An alternate method of the present invention uses a mined subterranean cavern shown in FIGS. 3 and 4 to promote plug flow and thus permit shorter residence time. A number of generally horizontal chambers 70 are mined from a suitable subterranean rock formation 72 by drilling and casing shafts 74 to a suitable depth, typically from two hundred to two thousand feet below the surface. The shafts 74 are then cleared of water and conventional hoists installed in them for transporting miners, equipment and supplies to the area to be mined. The generally horizontal chambers or drifts 70 are then mined out using, for example, the conventional mine, blast and muck technique. In this technique, bench headings are drilled, explosives installed and the rock face is blasted. Rubble produced is then transported to the surface for disposal. A suitable number of baffles 78 are located along the length of the drifts 70, for reasons to be set forth. Further, it is desirable that the drifts 70 slope gently upwardly from the shafts 74, typically on the order of a five percent slope. It should be understood that other percentage slopes could equally as well be used, depending on site conditions, with ranges of from about three percent to about ten percent being generally acceptable.

A transversely extending tunnel 80 is mined or formed to connect inner end portions of aligned drifts 70. A main pump out shaft 82 is formed at each end of the tunnel 80 and a submersible pump 84 is installed in an inner casing 86 to pump protein broth or liquid from the tunnel 80 and drifts 70. An outer casing 88 permits gases produced from the bioreaction which accumulate in an upper portion of the inner ends of drifts 70 and tunnel 80 to be pumped out by a pump of the type shown in FIGS. 1 and 2. A number of pump out wells 90 are formed along the length of the tunnel 80 so that gas and liquid produced in the drifts 70 and tunnel 80 may be extracted and transported to the surface.

In the embodiment of FIGS. 3 and 4, sixteen drifts 70 are shown, each approximately two hundred twenty feet in length. The drifts 70 are about forty feet by forty feet in vertical cross-section in the embodiment shown. This is given only as an example, since length to diameter ratios of from 5:1 to 100:1 may be used depending on process output requirements and geological conditions at the site. The main shafts 82 are located approximately eight hundred feet from each other. The number of pump out wells 90 can range from the three shown to as many as eight or ten, according to process output capacity.

After the drifts 70 have been mined and the baffles 78 installed, a portion of the rubble produced during mining operations is crushed to a suitable size, such as one inch by two inches or so. The crushed rubble so produced is then packed into the drifts 70 to serve as a substrate for the biochemical reaction, which functions as an anaerobic fixed film process. As alternatives to crushed formation rock, gravel or synthetic resin particles or other suitable particles may be used to pack the drifts 70. The packing material can be considered an anaerobic filter.

Alternatively, the reaction may take place in either the form of what is known as a sludge blanket or an expanded bed or fluidized bed anaerobic fixed flim digester. In the sludge blanket, a floc of microorganisms occurs and is maintained, further entrapping newly formed microorganisms. In the expanded bed or fluidized bed designs, the particles used for microorganism attachment are of a size and density, relative to the aqueous fermenter fluid, such that they expand or become fluidized. This permits less clogging of the bed by any suspended debris.

The input feed stock of inoculated organic fluid solution is then injected into the drifts 70 from injection wells in the shafts 72, travelling through the drifts 70 in a plug flow reaction. The packed drifts 76 function as packed bed bioreactors, with the baffles 78 functioning to increase the flow rate of the reacting fluid solution and promote plug flow.

While the preferred methods are illustrated in the foregoing description, many variations in the size, shape and materials, as well as in the details of the illustrated method, will occur to those skilled in the art. It is intended that all such variations which fall within the scope and spirit of the appended claims be embraced thereby.

We claim:

1. A method for biochemically converting coal to combustible hydrocarbon gases, comprising the steps of:
   (a) treating the coal by contacting the coal in a finely divided state with a hot aqueous alkali solution at a temperature of from about 150° C. to about 300° C. to produce an aqueous mixture of low molecular weight organics;
   (b) feeding the organic solution or mixture into a subterranean cavity;
   (c) inoculating the organic solution or mixture with a methanogenic microorganism culture;
   (d) maintaining the inoculated organic solution or mixture in the cavity at a pH between about 6.5 and about 8.5 and at a temperature between about 10° C. and about 60° C.;
   (e) allowing the microorganisms to grow in the organic solution or mixture in the cavity to produce methane; and
   (f) recovering the produced combustible hydrocarbon gases from the cavity.

2. The method of claim 1, further including the step of:
   maintaining continuously stirred tank reactor conditions in the inoculated organic solution in the cavity.

3. The method of claim 1, further including the step of:
   maintaining plug flow conditions in the inoculated organic solution in the cavity.

4. The method of claim 1 further including the step of:
   inoculating the organic solution or mixture with acid formers in a first reactor prior to said step of inoculating with a methanogenic microorganism culture.

5. The method of claim 4, further including the step of:
   introducing the output of the first reactor into the cavity during said step of inoculating with a methanogenic microorganism culture.

6. The method of claim 1, further including the step of:
   packing the cavity with particles prior to said step of feeding the organic solution into the cavity.

7. The method of claim 6, wherein:
the particles packing the cavity are of a size and density so as to allow them to expand and become fluidized to permit less clogging with debris.

8. The method of claim 1, further including the step of:
maintaining the microorganisms in the form of a floc in the cavity to trap newly formed microorganisms.

* * * * *

UNITED STATES PATENT AND TRADEMARK OFFICE
CERTIFICATE OF CORRECTION

PATENT NO. : 4,845,034

DATED : July 4, 1989

INVENTOR(S) : William M. Menger, Ernest E. Kern, Kermit Allen, et al.

It is certified that error appears in the above-identified patent and that said Letters Patent is hereby corrected as shown below:

Col. 6, line 35, please delete "is" and insert --if-- therefor.

Col. 9, line 52, please delete "10°-20%" and insert --10-20%-- therefor.

Signed and Sealed this

Fifteenth Day of May, 1990

Attest:

HARRY F. MANBECK, JR.

Attesting Officer    Commissioner of Patents and Trademarks